ns Patent [19]

Cozzi et al.

[11] 4,302,472
[45] Nov. 24, 1981

[54] SUBSTITUTED N-(β-ALKOXY-ETHYL)-N-(4-PHENOXY-BENZYL)-DICHLORO-ACETAMIDES AND PROCESS FOR THEIR PREPARATION

[75] Inventors: Paolo Cozzi, Milan; Piero Menchetti, Lucca; Ivo de Carneri; Franca Trane, both of Milan, all of Italy

[73] Assignee: Farmitalia Carlo Erba S.p.A., Milan, Italy

[21] Appl. No.: 62,740

[22] Filed: Aug. 1, 1979

Related U.S. Application Data

[63] Continuation of Ser. No. 939,208, Dec. 5, 1978, abandoned.

[30] Foreign Application Priority Data

Oct. 3, 1977 [IT] Italy ................................ 28197 A/77
Aug. 4, 1978 [IT] Italy ................................ 26464 A/78
Aug. 4, 1978 [IT] Italy ................................ 26465 A/78
Aug. 4, 1979 [IT] Italy ................................ 26466 A/78

[51] Int. Cl.³ .................... A61K 31/165; C07C 97/16; C07C 103/10; C07C 103/32
[52] U.S. Cl. ..................................... 424/324; 424/300; 564/152; 564/154; 564/155; 564/157; 564/158

[58] Field of Search ................................ 424/324, 300; 260/562 B, 562 S, 564 N; 564/152, 154, 155, 157, 158

[56] References Cited

U.S. PATENT DOCUMENTS 2,824,894  2/1958  Logemann et al. ................. 260/562
3,658,967  4/1972  Leigh et al. ......................... 424/324

FOREIGN PATENT DOCUMENTS 553339  12/1956  Belgium .
2207246  8/1972  Fed. Rep. of Germany ...... 424/324

OTHER PUBLICATIONS

Chem. Abst. 52, 2000(h)-Logemann et al. (1958),
Chem. Abst. 55, 13656(g)-Carneri et al.(1961).
Chem. Abst. 53, 20586(i)-Carneri et al.(1959).
Chem. Abst. 53, 5519(c)-Carneri (1959).

Primary Examiner—Douglas W. Robinson
Attorney, Agent, or Firm—Murray and Whisenhunt

[57] ABSTRACT

Substituted N-(β-Alkoxy-Ethyl)-N-(4-Phenoxy Benzyl)-Dichoroacetamides are provided for the chemotherapeutic treatment of amebiasis.

8 Claims, No Drawings

SUBSTITUTED N-(β-ALKOXY-ETHYL)-N-(4-PHENOXY-BENZYL)-DICHLORO-ACETAMIDES AND PROCESS FOR THEIR PREPARATION

This is a continuation application of Ser. No. 939,208, filed Sept. 5, 1978, now abandoned.

The present invention relates to substituted N-(β-alkoxy-ethyl)-N-(4-phenoxy-benzyl)-dichloroacetamides, to a process for their preparation and to pharmaceutical and veterinary compositions containing them. The compounds of the invention have the following general formula (1)

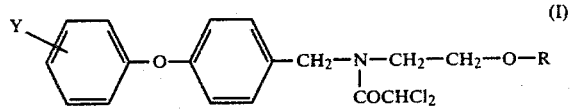

wherein
R is $C_1$–$C_6$ alkyl;
Y is
(a)

wherein each of R' and R", which may be the same or different, is hydrogen or $C_1$–$C_6$ alkyl;
(b)

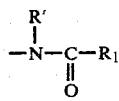

wherein R' is as defined above and $R_1$ is: (a') $C_1$–$C_{12}$ alkyl unsubstituted or substituted by one or more substituents selected from the group consisting of halogen, cyano, carboxy, carbamoyl, methylthio, —OR', wherein R' is as defined above,

wherein R' and R" are as defined above, and phenyl unsubstituted or substituted by one or more hydroxy groups; (b') phenyl unsubstituted or substituted by one or more substituents selected from the group consisting of halogen, cyano, $C_1$–$C_6$ alkyl, trihalo-$C_1$–$C_6$-alkyl, nitro, —OR' and

wherein R' and R" are as defined above;
(c)

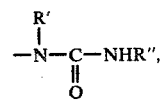

wherein R' and R" are as defined above;
(d)

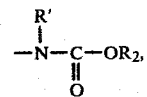

wherein R' is as defined above and $R_2$ is $C_1$–$C_4$ alkyl;
(e) —$SO_2R_2$, wherein $R_2$ is as defined above.

Object of the present invention are also the pharmaceutically or vertically acceptable salts of the compounds of formula (1) as well as all the possible isomers and their mixtures, the metabolites provided with pharmacological activity and the metabolic precursors of the compounds of formula (1), as well as the pharmaceutical and veterinary compositions containing the compounds of formula (1) or their salts. The alkyl groups may be branched or straight chain groups. A halogen atom is preferably fluorine, chlorine or bromine. A trihalo-$C_1$–$C_6$-alkyl group is preferably a trihalo-methyl group, in particular trifluoromethyl.

When $R_1$ is a $C_1$–$C_{12}$ alkyl group optionally substituted as reported above, it is preferably an optionally substituted $C_1$–$C_6$ alkyl group.

Examples of pharmaceutically or veterinarily acceptable salts of the compounds of formula (1) are either the salts with inorganic acids, e.g. nitric, hydrochloric, hydrobromic, sulphuric and phosphoric acids, or with organic acid, e.g. acetic, propionic, glycolic, lactic, maleic, fumaric, malic, tartaric, citric, benzoic, cinnamic, mandelic, salicylic, succinic, methanesulphonic, ethanesulphonic and stearic acids, or the salts with inorganic bases, e.g. the alkaline, e.g. sodium or potassium, or alkaline-earth, e.g. calcium, hydroxides, or with organic bases, e.g. triethylamine, diethylamine, N-ethyl-piperidine, dibenzylamine, and other acceptable organic amines.

Preferred compounds of the invention are the compounds of formula (1) wherein R is $C_1$–$C_3$ alkyl; Y is (a)

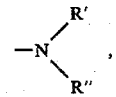

wherein each of R' and R'", which may be the same or different, is hydrogen or $C_1$–$C_6$ alkyl; (b)

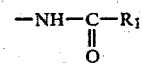

wherein $R_1$ is (a') $C_1$–$C_6$ alkyl unsubstituted or substituted by one or more substituents selected from the group consisting of halogen, methylthio, carboxy, carbamoyl, unsubstituted phenyl, hydroxy or amino or (b') phenyl; (c)

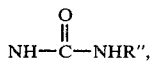

wherein R″ is hydrogen or $C_1$–$C_3$ alkyl; (d)

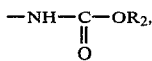

wherein $R_2$ is $C_1$–$C_3$ alkyl or (e) —$SO_2R_2$, wherein $R_2$ is $C_1$–$C_3$ alkyl, as well as their pharmaceutically and veterinarily acceptable salts.

Examples of particularly preferred compounds of the invention are:

N-(β-ethoxy-ethyl)-N-[4-phenoxy-(4′-amino)-benzyl]-dichloroacetamide;
N-(β-methoxy-ethyl)-N-[4-phenoxy-(4′-amino)-benzyl]-dichloroacetamide;
N-(β-ethoxy-ethyl)-N-[4-phenoxy-(4′-methylamino)-benzyl]-dichloroacetamide;
N-(β-ethoxy-ethyl)-N-[4-phenoxy-(4′-dimethylamino)-benzyl]-dichloroacetamide;
N-(β-ethoxy-ethyl)-N-[4-phenoxy-(4′-ethylamino)-benzyl]-dichloroacetamide;
N-(β-ethoxy-ethyl)-N-[4-phenoxy-(4′-n-butylamino)-benzyl]-dichloroacetamide;
N-(β-ethoxy-ethyl)-N-[4-phenoxy-(4′-acetamido)-benzyl]-dichloroacetamide;
N-(β-ethoxy-ethyl)-N-[4-phenoxy-(4′-chloroacetamido)-benzyl]-dichloroacetamide;
N-(β-ethoxy-ethyl)-N-[4-phenoxy-(4′-dichloroacetamido)-benzyl]-dichloroacetamide;
N-(β-ethoxy-ethyl)-N-[4-phenoxy-(4′-trifluoroacetamido)-benzyl]-dichloroacetamide;
N-(β-ethoxy-ethyl)-N-[4-phenoxy-(4′-propionylamino)-benzyl]-dichloroacetamide;
N-(β-ethoxy-ethyl)-N-[4-phenoxy-(4′-pivaloylamino)-benzyl]-dichloroacetamide;
N-(β-ethoxy-ethyl)-N-[4-phenoxy-(4′-benzoylamino)-benzyl]-dichloroacetamide;
N-(β-ethoxy-ethyl)-N-[4-phenoxy-(4′-glycinylamino)-benzyl]-dichloroacetamide;
N-(β-ethoxy-ethyl)-N-[4-phenoxy-(4′-norvalinylamino)-benzyl]-dichloroacetamide;
N-(β-ethoxy-ethyl)-N-[4-phenoxy-(4′-alanylamino)-benzyl]-dichloroacetamide;
N-(β-ethoxy-ethyl)-N-[4-phenoxy-(4′-valinylamino)-benzyl]-dichloroacetamide;
N-(β-ethoxy-ethyl)-N-[4-phenoxy-(4′-leucinylamino)-benzyl]-dichloroacetamide;
N-(β-ethoxy-ethyl)-N-[4-phenoxy-(4′-β-lanylamino)-benzyl]-dichloroacetamide;
N-(β-ethoxy-ethyl)-N-[4-phenoxy-(4′-γ-aminobutyrylamino)-benzyl]-dichloroacetamide;
N-(β-ethoxy-ethyl)-N-[4-phenoxy-(4′-lysinylamino)-benzyl]-dichloroacetamide;
N-(β-ethoxy-ethyl)-N-[4-phenoxy-(4′-serinylamino)-benzyl]-dichloroacetamide;
N-(β-ethoxy-ethyl)-N-[4-phenoxy-(4′-methionylamino)-benzyl]-dichloroacetamide;
N-(β-ethoxy-ethyl)-N-[4-phenoxy-(4′-tyrosinylamino)-benzyl]-dichloroacetamide;
N-(β-ethoxy-ethyl)-N-[4-phenoxy-(4′-aspartylamino)-benzyl]-dichloroacetamide;
N-(β-ethoxy-ethyl)-N-[4-phenoxy-(4′-asparagylamino)-benzyl]-dichloroacetamide;
N-(β-ethoxy-ethyl)-N-[4-phenoxy-(4′-glutamylamino)-benzyl]-dichloroacetamide;
N-(β-ethoxy-ethyl)-N-[4-phenoxy-(4′-glutaminylamino)-benzyl]-dichloroacetamide;
N-(β-ethoxy-ethyl)-N-[4-phenoxy-(4′-lactoylamino)-benzyl]-dichloroacetamide;
N-(β-ethoxy-ethyl)-N-[4-phenoxy-(4′-hydroxyacetamido)-benzyl]-dichloroacetamide;
N-(β-ethoxy-ethyl)-N-[4-phenoxy-(4′-α-hydroxybutyrylamino)-benzyl]-dichloroacetamide;
N-(β-ethoxy-ethyl)-N-[4-phenoxy-(4′-ureido)-benzyl]-dichloroacetamide;
N-(β-ethoxy-ethyl)-N-{4-phenoxy-[4′-(N-ethyl-carbamoyl)-amino]-benzyl}-dichloroacetamide;
N-(β-ethoxy-ethyl)-N-{4-phenoxy-[4′-(N-methylcarbamoyl)-amino]-benzyl}-dichloroacetamide;
N-(β-ethoxy-ethyl)-N-[4-phenoxy-(4′-ethoxycarbonylamino)-benzyl]-dichloroacetamide;
N-(β-ethoxy-ethyl)-N-[4-phenoxy-(4′-methylsulphonyl)-benzyl]-dichloroacetamide, as well as the pharmaceutically or vertinarily acceptable salts thereof.

The compounds of the invention are prepared by a process comprising:

(A) reducing a compound of formula (II)

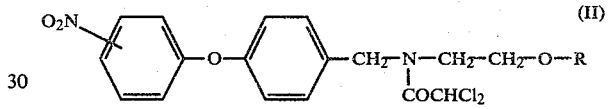

wherein

R is as defined above, so obtaining compounds of formula (I) wherein Y is amino and, if desired, alkylating a compound of formula (I) wherein Y is amino so obtaining compounds of formula (I) wherein Y is

wherein R′ and R″ are as defined above, at least one of them being different from hydrogen; or (B) acylating a compound of formula (III)

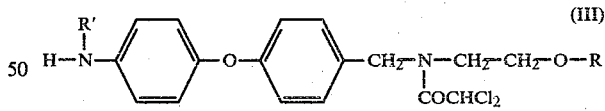

wherein

R and R′ are as defined above, with a compound of formula (IV)

wherein $R_1$ is as defined above, or a reactive derivative thereof, so obtaining compounds of formula (I) wherein Y is

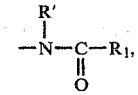

wherein R' and R₁ are as defined above; or (C) reacting a compound of formula (III), or a salt thereof, with a compound of formula (V)

$$R_3-N=C=O \qquad (V)$$

wherein

R₃ is C₁-C₆ alkyl, an alkaline cation, or —ClSO₂, so obtaining compounds of formula (I) wherein Y is

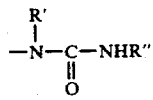

wherein R' is as defined above and R'' is C₁-C₆ alkyl or hydrogen; or (D) reacting a compound of formula (III), with a compound of formula (VI)

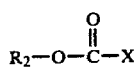

wherein

X is halogen and R₂ is as defined above, so obtaining compounds of formula (I) wherein Y is

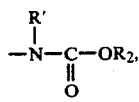

wherein R' and R₂ are as defined above; or (E) reacting a compound of formula (VII)

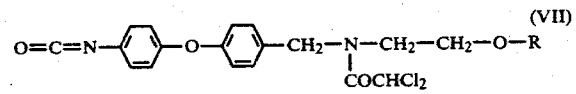

wherein

R is as defined above, with a compound of formula (VIII)

$$R_4-Z \qquad (VIII)$$

wherein

Z is amino or hydroxy and wherein, when Z is amino, R₄ is hydrogen or C₁-C₆ alkyl, or, when Z is hydroxy, R₄ is C₁-C₄ alkyl, so obtaining compounds of formula (I) wherein Y is

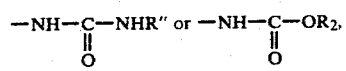

wherein R'' and R₂ are as defined above; or (F) reacting a compound of formula (IX

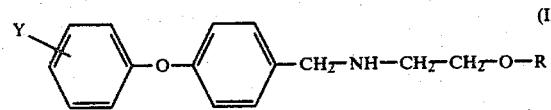

wherein

R and Y are as defined above, or a salt thereof, with dichloroacetic acid, or a reactive derivative thereof and, if desired, converting a compound of formula (I) into another compound of formula (I) and/or, if desired, salifying a compound of formula (I) and/or, if desired, obtaining a free compound from a salt and/or, if desired, resolving a mixture of isomers into the single isomers.

The reduction of a compound of formula (II) to give a compound of formula (I) wherein Y is amino may be, for example, carried out either in an acidic medium, e.g. SnCl₂ and hydrochloric acid or Zn and glacial acetic acid, or in a neutral or alkaline medium, e.g. bivalent sulphur derivatives, for instance ammonium or alkaline, e.g. sodium or potassium, sulphides, hydrosulphites or hydrosulphides which, if desired, may be prepared in situ; or by reaction with TiCl₃, preferably at 15% aqueous solution of TiCl₃, in a suitable solvent such as, e.g., acetone, ethyl acetate, methyl or ethyl alcohol and benzene; or by treatment with iron powder in the presence of ammonium chloride, in a suitable solvent such as, e.g., chlorobenzene; or by catalytic hydrogenation in the presence of a catalyst which may be, for example, palladium or Raney Nickel, in a solvent selected, e.g., from the group consisting of methyl or ethyl alcohol, acetic acid, cyclohexane, ethyl acetate, benzene, toluene, at a pressure ranging from the atmospheric pressure to about 50 atmospheres. The optional alkylation of a compound of formula (I) wherein Y is amino to give a compound of formula (I) wherein Y is

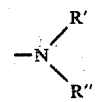

wherein R' and R'' are as defined above, at least one of them being different from hydrogen, may be carried out either by alkylation or by reductive alkylation.

The alkylation may be performed, for example, by reaction with the appropriate C₁-C₆ alkyl halide, preferably chloride, bromide, iodide, preferably in the presence of a base, such as, for instance, an organic tertiary amine, e.g. triethylamine or piperidine, or by reaction with a reactive ester, e.g. mesylate or tosylate, of a C₁-C₆ aliphatic alcohol or with a C₁-C₆ aliphatic alcohol in the presence, if necessary, of an acid catalyst, such as, e.g., gaseous hydrochloric acid or boron trifluoride. In these cases the alkylation, which is preferably performed in an inert organic solvent such, e.g., benzene, toluene, dimethylformamide or, if desired, using a mixture of the alkylating agent as solvent, at a temperature varying between the room and the reflux temperature of the used solvent, leads to compounds of formula (I) wherein Y is

wherein one of R' and R'' is hydrogen and the other is C₁-C₆ alkyl or both R' and R'', being the same, are C₁-C₆ alkyl.

The alkylation may also be performed, if desired, by reacting a compound of formula (I) wherein Y is amino with a C₁-C₆ alkyl orthoformate at a temperature sufficient to distill off the liberated C₁-C₆ aliphatic alcohol, then hydrolyzing under mild reaction conditions, e.g. with hydroalcoholic solutions of 0,5 N HCl or with 15% hydrogen peroxide, the intermediate N-formyl-N-($C_1$-$C_6$)-alkyl derivative, so obtaining compounds of formula (I) wherein Y is

wherein one of R' and R" is hydrogen and the other is $C_1$-$C_6$ alkyl.

Alternatively the alkylation may be effected, e.g., reacting a compound of formula (I) wherein Y is amino with a $C_1$-$C_6$ trialkylphosphate at temperatures ranging preferably from about 80° C. to about 160° C., then submitting the reaction mixture to a mild, preferably alkaline, hydrolysis, so obtaining compounds of formula (I) wherein Y is

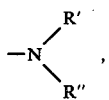

wherein R' and R", being the same, are both $C_1$-$C_6$ alkyl. The reductive alkylation may be effected, for example, by reacting a compound of formula (I) wherein Y is amino with an appropriate carbonyl compound, preferably a $C_1$-$C_6$ aliphatic aldehyde, in the presence of a reducing agent, e.g. hydrogen and a catalyst, using, e.g., the same reaction conditions hereabove reported for the catalytic hydrogenation of a compound of formula (II), so obtaining compounds of formula (I) wherein Y is

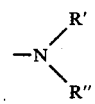

wherein R' is hydrogen and R" is $C_1$-$C_6$ alkyl or R' and R", being the same, are both $C_1$-$C_6$ alkyl.

The reductive alkylation may also by carried out, if desired, at the same time with the reduction, e.g. by catalytic hydrogenation, of the compound of formula (II) by adding the desired carbonyl compound to the reaction mixture during the reduction process.

A reactive derivative of an acid of formula (IV) may be for example, an halide, e.g. chloride or bromide, an anhydride, e.g. a mixed anhydride, a reactive ester or an azide.

The acylation of a compound of formula (II) with a compound of formula (IV), or a reactive derivative thereof, may be effected by conventional methods, for example at room temperature or under cooling in a solvent such as, for instance, acetone, dioxane, tetrahydrofurane, acetonitrile, chloroform, methylenechloride or a mixture of said solvents or using an excess of the reactive derivative of the compound of formula (IV) as solvent, in the presence, if necessary, of a base such as, for example, an alkaline, e.g. sodium or potassium, bicarbonate or a trialkylamine, e.g. triethylamine. When a compound of formula (III) is reacted with a free acid of formula (IV) the acylation is preferably carried out in the presence of a condensing agent, such as, e.g., dicyclohexylcarbodiimide. When in the compound of formula (IV) functional groups are present which may interfere in the acylation process, e.g. amino or hydroxy or a further carboxy group, these groups are preferably protected, in a conventional way, before the reaction by means of protecting groups easily removable at the end of the acylation.

The protection of the amino groups may be effected, for example, by the known protecting groups usually employed in the synthesis of peptides, e.g. t-butoxycarbonyl, benzyloxycarbonyl, p-methoxybenzyloxycarbonyl, o-nitrophenylsulphenyl, formyl, trifluoroacetyl, o-hydroxybenzilidene, t-butyldimethylsilyl, or by protonation, e.g. by salification with strong, preferably mineral, acids, e.g. hydrochloric acid, or also by conversion of the amino-compound into an enaminoderivative, for example by reaction with a $\beta$-dicarbonyl compound, e.g. acetoacetone or ethyl-$\beta$-acetoacetate.

The hydroxy groups may be protected in a conventional manner, for example by the protecting groups usually employed for the protection of the alcoholic function, e.g. formyl, dichloroacetyl, tetrahydropyranyl or $\beta$-methoxy-ethoxymethyl.

Also the protection of a second carboxy group, if present in the compound of formula (IV), may be effected by known procedure, using as protecting groups, e.g., the groups t-butyl, benzhydryl or p-methoxybenzyl. The protecting groups, e.g. those mentioned above, may be removed at the end of the reaction in a conventional way, e.g. by mild acidic or basic hydrolysis or by mild catalytic reduction, for example by hydrogenation at atmospheric pressure in the presence of Pd/C as catalyst. In particular when the protonation is used to protect the amino group, the salifying acid may be removed by treatment with a base such as, e.g., an alkaline, in particular sodium or potassium, carbonate or bicarbonate, and when the $\beta$-methoxy-ethoxymethyl group is used to protect the hydroxy group, the protecting group may be removed by treatment with metallic halides, preferably chlorides, e.g. $ZnCl_2$, $FeCl_2$ or $TiCl_3$, in an inert organic solvent, such as, e.g. methylene chloride. A salt of a compound of formula (III) may be, for example, a salt with a mineral acid, e.g. the hydrochloride or the hydrobromide.

When in a compound of formula (V) $R_3$ is an alkaline cation, it is preferably potassium.

The reaction between a compound of formula (III) and a compound of formula (V) may be effected by known procedures, for instance, at room temperature or under cooling in an inert organic solvent, e.g. benzene, toluene, methylene chloride, chloroform, acetone or a mixture of said solvents, when in the compound of formula (V) $R_3$ is $C_1$-$C_6$ alkyl; or, for example, at temperatures ranging between the room temperature and about 50° C. in aqueous acidic solutions, e.g. diluted acetic acid, when in the compound of formula (V) $R_3$ is an alkaline cation. Instead, when $R_3$ is the radical —$ClSO_2$, the reaction may be performed, for example, at temperatures ranging from about —10° C. and the room temperature, in inert solvents such as, for example, acetonitrile, tetrahydrofuran, acetone, submitting the obtained chlorosulphonylureido derivatives to hydrolysis in presence of diluted mineral acids, for example diluted $H_2SO_4$. In the compound of formula (VI) X is preferably chlorine. The reaction of a compound of formula (III), with a compound of formula (VI) may be carried out by conventional methods, e.g. at temperatures ranging from about —10° C. to about 25° C. in the presence of a base such as, e.g., an alkaline, e.g. sodium or potassium bicarbonate, or a dialkylamine, e.g. triethylamine, in an inert organic solvent, such as, for instance, acetone, methylene chloride, chloroform, benzene, tetrahydrofurane, or a mixture of said solvents.

The reaction between a compound of formula (VII) and a compound of formula (VIII) may be performed by known methods, for example at room temperature or under cooling, preferably at a temperature varying from about $-10°$ C. to about 25° C., in aqueous or organic solvents, such as, e.g. water, $C_1-C_6$ aliphatic alcohols, benzene, toluene, methylene chloride, preferably by adding the compound of formula (VIII) to the compound of formula (VII).

A salt of a compound of formula (IX) may be, for example, a salt with inorganic acids, preferably the hydrochloride or the hydrobromide. A reactive derivative of dichloroacetic acid may be one of the reactive derivatives indicated above for the acid of formula (IV), i.e. an halide, an anhydride, e.g. a mixed anhydride, a reactive ester or an azide, preferably being an halide.

The reaction between a compound of formula (IX), or a salt thereof, and dichloroacetic acid, or a reactive derivative thereof, may be carried out by the same procedure described above for the acylation of a compound of formula (III) with a compound of formula (IV). Also in this case functional groups, eventually present in the compound of formula (IX), which may interfere in the reaction, e.g. amino or hydroxy or carboxy groups, are preferably protected before the reaction by the same protecting groups already indicated, the protecting groups being then removed at the end of the reaction by mild conditions as reported above. The compounds of formula (I) wherein protecting groups, e.g. those mentioned above, are present, are also included in the object of the present invention.

The optional conversion of a compound of formula (I) into another compound of formula (I) may be carried out by conventional methods.

Thus, for example, a compound of formula (I) wherein Y is

wherein R' is hydrogen and R" is $C_1-C_6$ alkyl may be converted into a compound of formula (I) wherein R' and R" are both $C_1-C_6$ alkyl, R' being different from R", by alkylation according to known methods, e.g. by the procedures reported above for the alkylation of a compound of formula (I) wherein Y is amino.

For example, $C_1-C_6$ alkoxy groups may be converted into free hydroxy groups by deetherification, e.g. by treatment with pyridine hydrochloride or boron tribromide according to conventional procedures.

Also the optical salification of a compound of formula (I) as well as the conversion of a salt of a compound of formula (I) into the free compound and the separation of a mixture of isomers into the single isomers may be effected by the conventional methods of the organic chemistry.

For example, the single optical isomers may be obtained from a racemic mixture by treatment with an appropriate optically active acid or base then separating the obtained diastereoisomeric salts, e.g. by chromatography or by fractionate crystallization, and finally liberating the single optional isomers from the separated diastereoisomeric salts, e.g. by alkalization or acidification.

The compounds of formula (II) are either known compounds, ["| | Farmaco" Ed. Sci., 13, 139, (1958)], or may be prepared by known methods, e.g. by the method described in the hereabove cited reference.

The compounds of formula (III) are compounds of the invention and may be prepared as already described in this specification, i.e. reducing compounds of formula (II) and, if desired, alkylating the obtained compounds of formula (I) wherein Y is amino.

The compounds of formula (IV), (V) and (VI) are known compounds.

The compounds of formula (VII) may be prepared, e.g. by reacting a compound of formula (I) wherein Y is amino with phosgene in a suitable anhydrous inert organic solvent, e.g. toluene or methylene chloride, under cooling, preferably at temperatures varying from about $-30°$ C. to about 0° C., in the presence of a basic agent, such as, for example, a trialkylamine, e.g. triethylamine.

The compounds of formula (VIII) are known compounds. The compounds of formula (IX) may be prepared by reacting a compound of formula (X)

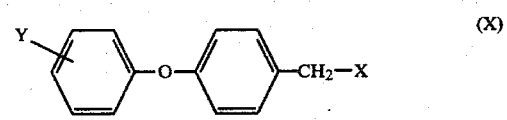

wherein

Y and X are as defined above, X preferably being bromine or chlorine, with the appropriate $\beta-C_1-C_6$-alkoxy ethylamine according to the methods usually employed for the alkylation of the amines.

The compounds of formula (X) may be prepared:

(a") halogenating a compound of formula (XI)

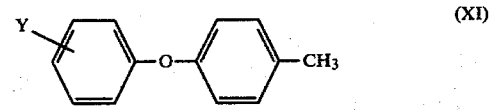

wherein Y is as defined above; or (b") halomethylating a compound of formula (XII)

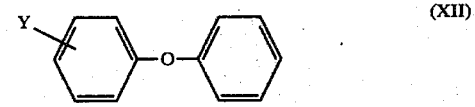

wherein Y is as defined above; or (c") converting an alcohol of formula (XIII)

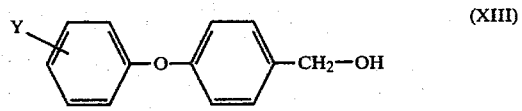

wherein Y is as defined above, into the corresponding halide.

The halogenation of a compound of formula (XI) may be carried out by known methods, e.g. by bromination with N-bromo-succinimide or by chlorination with N-chloro-succinimide. The halomethylation of a compound of formula (XII) may be effected in a conventional manner, preferably by chloromethylation, e.g.

with formaldehyde or trioxymethylene and hydrochloric acid in the presence, when necessary, of a metallic halide, e.g. $ZnCl_2$, as catalyst.

Also the conversion of an alcohol of formula (XIII) into the corresponding halide may be carried out in a conventional way, e.g. by treatment with $SOCl_2$ or another acid halide, e.g., $PCl_3$, $POCl_3$ or $PBr_3$.

The compounds having the formulae (XI), (XII) and (XIII) are known compounds or may be prepared by known methods. In particular the alcohols of formula (XIII) may be obtained by reducing the corresponding carboxylic acids, e.g. with diborane, or the lower alkyl esters thereof, e.g. with $LiAlH_4$, by conventional procedures.

The compounds of the invention are endowed with antiamebic activity. The antiamebic activity expressed as minimal sterilizing concentration is comprised between 0.003 and 0.3 μg/ml and is higher in vitro and in vivo than that of other dichloroacetamide derivatives used in therapy.

These new compounds are therefore useful for the chomotherapy of intestinal infections due to *Entamoeba histolytica* both in patients with acute amebiasis and in patients with chronic amebiasis; furthermore, they are also useful for the chomoprophylaxis of amebiasis in the areas in which this parasitosis is endemic.

The following methods were employed for evaluation of antiamebic activity in vitro and in vivo:

1. in vitro

The in vitro activity on Entamoeba histolytica Meah was determined on the products under test and on reference compounds, by the method of serial dilutions (ratio 1:1.5) in monophasic Pavlova medium with inoculation of 30,000 protozoa/ml and with incubation at 37° C. for 48 hours.

The level of activity of the compounds was determined by means of direct microscopical examination at 125 and 500 magnifications of the entire sediment of each culture. The results were expressed as minimal amoebicidal concentration in μg/ml.

2. in vivo

The in vivo antiamebic activity in the intestinal infection was determined with a method similar to the method described by Jones (Ann.trop.Med.Paras., 40, 130–140, 1946), as reported hereunder. Young, specific pathogen free albino rats (strain:Wistar CFHB) weighing 30–35 g and fed on a low-protein diet, were infected by intracecal injection with a suspension of trophozoites of Entamoaba histolytica Meah (250,000/rat) containing 3% of Wilson gastrin mucin. The substances under test and the reference products were administered in serial doses, by gavage twice a day for 2½ days. The therapeutic effect was determined on the fifth day after infection on the basis of the presence or absence of amebic ulcers in the cecal mucosa and of viable amoebae in the cecal mucosa and in the fecal content of the cecum.

Each animal was assigned a score, according to the following scale:

score 0 = no amoebae, no ulceration;
score 1 = from 1 to 20 amoebae per faecal smear; no amoeba in the scrape of caecal mucosa; no ulceration;
score 2 = from 20 to a very large number of amoebae per smear of feces; no ameoba in the mucosal scrape; no ulceration;
score 3 = amoebae originating from microscopic lesions of the cecal mucosa;
score 4 = microscopic lesions of the cecal mucosa;
score 5 = more than half the cecum ulcerated by amoebic lesions.

The antiamebic activity was expressed both as $ED_{50}$ calculated according to the number of animals totally free of amoebae (score=0) and as mean score for each dose level.

The in vitro and in vivo results are reported in Tables 1 and 2.

TABLE 1

In vitro activity expressed as minimal amoebicidal concentration in μg/ml.

| Dosage | Compound A* | Compound B** | Eto-famide | Diloxanide furoate | Tec-lozan |
|---|---|---|---|---|---|
| I | 0.017 | 0.004 | 0.026 | 0.44 | 0.058 |
| II | 0.017 | 0.005 | 0.026 | 0.44 | 0.058 |
| III | 0.017 | 0.007 | 0.058 | 0.44 | 0.087 |
| IV | 0.026 | 0.013 | 0.058 | 0.29 | 0.058 |
| V | 0.011 | 0.017 | 0.026 | 0.29 | 0.087 |
| VI | 0.011 | 0.008 | 0.017 | 0.19 | 0.058 |
| VII | 0.026 | 0.003 | 0.039 | 0.29 | 0.087 |
| VIII | 0.017 | 0.026 | 0.017 | 0.19 | 0.087 |
| IX | 0.026 | 0.017 | 0.058 | 0.19 | 0.087 |
| X | 0.026 | 0.017 | 0.039 | 0.19 | 0.058 |
| mean | 0.019 | 0.011 | 0.036 | 0.30 | 0.072 |

*Compound A = N-(β-ethoxy-ethyl)-N-[4-phenoxy-(4'-amino)-benzyl]-dichloroacetamide
**Compound B = N-(β-ethoxy-ethyl)-N-[4-phenoxy-(4'-acetamido)-benzyl]-dichloroacetamide.

TABLE 2

In vivo activity in intestinal amebiasis in the rat.
The mean scores (20 animals) are reported for each dose administered, and the $ED_{50}$ calculated on the number of animals with score = 0.

| Administered dose mg/kg × 5 times | Mean Score (*) Compound A | Eto-famide | $ED_{50}$ mg/kg × 5 Compound A | Eto-famide |
|---|---|---|---|---|
| 6.2 | 1.6 | 3.3 | | |
| 12.5 | 1.1 | 1.6 | | |
| 25 | 1.0 | 1.3 | 19 | 29 |
| 50 | 0.5 | 1.0 | | |

(*) mean score of the control animals treated with vehicle only = 3.5.

Furthermore, the compounds of formula (I), wherein Y is an acylamino group, wherein the acyl bears at least an amino group and/or a hydroxy group, for example the compound N-(β-ethoxy-ethyl)-N-[4-phenoxy-(4'-glycinylamino)-benzyl]-dichloroacetamide, have the further advantage of being absorbed to a greater extent, and thus being active on amoebae within the intestinal wall itself.

The toxicity of the compounds of the invention is quite negligible. For example, for the compounds A and B mentioned in the foregoing Tables the approximate acute toxicity ($LD_{50}$) in the mouse, determined with single administration of increasing doses and measured on the seventh day of treatment, was, per os, much higher than 800 mg/kg. Similar $LD_{50}$ are found also for the other compounds of the invention, in particular for the compounds:

N-(β-ethoxy-ethyl)-N-[4-phenoxy-(4'-(S)-nor-valinylamino)-benzyl]-dichloroacetamide chloride;
N-(β-ethoxy-ethyl)-N-[4-phenoxy-(4'-glycinylamino)-benzyl]-dichloroacetamide;
N-(β-ethoxy-ethyl)-N-[4-phenoxy-(4'-(S)-methionylamino)-benzyl]-dichloroacetamide;
N-(β-ethoxy-ethyl)-N-[4-phenoxy-(4'-methylsulphonyl)-benzyl]dichloroacetamide.

Pharmaceutical formulations of these compounds are prepared conventionally; they may be, for example, tablets, sugar-coated pills, capsules, syrups, drops, suppositories or sterile solutions for injection.

Oral administration is preferred, and pharmaceutical compositions of choice contain diluents like lactose, dextrose, sucrose, manitol, sorbitol, cellulose; lubrificants like silica, talc, stearic acid, magnesium or calcium stearate, and/or polyethylene glycols. They may also contain binders like amides, gelatin, methylcellulose, carboxy-methylcellulose, gum arabic, polyvinylpyrrolidine; anti-aggregants like starches, alginic acid, alginates; effervescent mixtures, colorants; sweeteners; wetting agents like lecithin, polysorbate, lauryl sulfate.

The preferred oral dose for the treatment of adult intestinal amoebiasis involves 200–1000 mg of active ingredient (preferably 200–500 mg) from 1 to 3 times daily for 5–10 days.

IR spectra were measured in solid phase (KBr), Nujol ® solution or a suitable $CHCl_3$-like solution, using a Perking-Elmer 125 spectrophotometer. NMR spectra were ran preferably in DMSO-$d_6$ or in $CDCl_3$ using a Bruker HFX 90 NH=instrument. Rf values were determined from thin layer chromatography on 0.25 mm silica gel plates.

The following examples illustrate but do not limit this invention.

EXAMPLE 1

23 ml of a 15% solution of $TiCl_3$ was added to 1.6 g of N-(β-methoxy-ethyl)-N-[4-phenoxy-(4'-nitro)-benzyl]-dichloroacetamide, in 30 ml of acetone; the pH was then adjusted to 3 with 23% HCl. The resulting mixture was stirred at room temperature for 24 hours and then, with cooling, brought to pH 9 with concentrated ammonium hydroxide. The resulting precipitate was removed by filtration and washed with water. The filtrated was extracted several times with chloroform. The combined organic extract was then dried on $Na_2SO_4$ and evaporated to dryness to give 1.2 g of N-(β-methoxy-ethyl)-N-[4-phenoxy-(4'-amino)-benzyl]-dichloroacetamide, m.p. 100°–102° C.

Elemental analysis:
found: C 56.25; H 5.23; N 7.26; Cl 18.6; $C_{18}H_{20}N_2Cl_2O_3$ requires C 56.4; H 5.22; N 1.31; Cl 18.5.

IR ($CHCl_3$):
$\nu$(N—H) 3400–3350 cm$^{-1}$ $\nu$(C=O) 1680 cm$^{-1}$

T.L.C.:
mobile phase: $CHCl_3$:MeOH:$NH_4OH$ (32%) (190:10:1) $R_f$=0.60.

The starting material N-(β-methoxy-ethyl)-N-[4-phenoxy-(4'-nitro)-benzyl]-dichloroacetamide was prepared as follows: 25 ml of NaOH/1 N was added to a suspension of 3.46 g of N-(β-methoxy-ethyl)-4-phenoxy-(4'-nitro)-benzylamino hydrochloride, in 25 ml of dichloroethane. 1.5 ml of a solution of dichloroacetylchloride in 2 ml of dichloroethane was then slowly added to the resulting mixture under stirring at 0° C. The reaction mixture was stirred for 30 minutes at 0° C. and for 3 hours at room temperature.

The organic phase was separated, washed with $H_2O$, dried on $Na_2SO_4$ and evaporated to dryness. The residue, crystallized from diethyl ether, gave 3.14 g of N-(β-methoxy-ethyl)-N-[4-phenoxy-(4'-nitro)-benzyl]-dichloroacetamide, m.p. 116°–117° C.

Elemental analysis:
found: C 52.24; H 4.30; N 6.74; Cl 17.27; $C_{18}H_{18}N_2Cl_2O_5$ requires C 52.3; H 4.38; N 6.78; Cl 17.17;

IR ($CHCl_3$):
$\nu(NO_2)$ 1510 cm$^{-1}$; 1350 cm$^{-1}$, $\nu$(C=O) 1680 cm$^{-1}$.

The intermediate N-(β-methoxy-ethyl)-4-phenoxy-(4'-nitro)-benzylamino hydrochloride was obtained as follows:

16.8 g of methoxyethylamine was added under stirring at 10° C. to 15 g of 4-phenoxy-(4'-nitro)-benzylbromide.

After stirring for 3 hours at room temperature, 200 ml of $H_2O$ was added and the mixture was extracted with ethyl acetate. The organic phase was washed with $H_2O$ and evaporated to dryness. The residue, dissolved in 130 ml of ethyl acetate, was treated with a stream of gaseous HCl. The precipitate was filtered and crystallized from absolute ethanol to give 14.2 g of N-(β-methoxyethyl)-4-phenoxy-(4'-nitro)-benzylamino hydrochloride, m.p. 178°–180° C.

Elemental analysis:
found: C 56.49; H 5.68; N 8.24; Cl 10.38; $C_{16}H_{19}N_2ClO_2$ requires C 56.8; H 5.62; N 8.28; Cl 10.47.

EXAMPLE 2

180 ml of a 15% solution of $TiCl_3$ was added to 12 g of N-(β-ethoxyethyl)-N-[4-phenoxy-(4'-nitro)-benzyl]-dichloroacetamide, m.p. 105°–106° C. in 200 ml of acetone; the pH was then adjusted to 3 with 23% HCl. The resulting mixture was stirred at room temperature for 24 hours and then, with cooling, brought to pH 9 with concentrated ammonium hydroxide. The resulting precipitate was removed by filtration and washed with $CHCl_3$. The filtered was extracted several times with $CHCl_3$. The combined organic extract was then dried and evaporated under reduced pressure to give a solid residue.

Crystallization from benzene (60°–80° C.) afforded 7.5 g of N-(β-ethoxyethyl)-N-[4-phenoxy-(4'-amino)-benzyl]-dichloroacetamide, m.p. 96°–98° C.

Elemental analysis:
found: C 57.44; H 5.57; N 7.05; Cl 17.85. calculated for $C_{19}H_{22}N_2Cl_2O_3$: C 57.4; H 5.57; N 7.05; Cl 17.85.

T.L.C.:
mobile phase $CHCl_3$:MeOH (190:10) $R_f$=0.50.

IR ($CHCl_3$):
$\nu(NH_2)$ 3430, 3360 cm$^{-1}$
$\nu$(C=O) 1680 cm$^{-1}$

NMR ($CDCl_3$) δppm:
1.18—3H—t—J=6 Hz (O—$CH_2$—$\underline{CH_3}$) 4.97—2-H—s—(—$NH_2$)

6.6–7.16 9H series of doublets (aromatic H and —CO—$CHCl_2$). The starting material N-(β-ethoxyethyl)-N-[4-phenoxy-(4'-nitro)-benzyl]-dichloroacetamide was prepared using the same procedure of Example 1 for the preparation of N-(β-methoxy-ethyl)-N-[4-phenoxy-(4'-nitro)-benzyl]-dichloroacetamide.

EXAMPLE 3

A solution of 2.5 g of N-(β-ethoxyethyl)-N-[4-phenoxy-4'-amino)-benzyl]-dichloroacetamide in 30 ml of anhydrous pyridine and 10 ml of acetic anhydride was held at room temperature for 24 hours. The reaction mixture was then brought to small volume under reduced pressure and taken up in water. The solid which formed was washed with slightly acid water, filtered, dried and triturated with ethyl ether to give 2.3 g N-(β-ethoxyethyl)-N-[4-phenoxy-(4'-acetamido)-benzyl]-dichloroacetamide, m.p. 114°-116° C.

Elemental analysis:
found: C 57.48; H 5.54; N 6.35; Cl 16.11.
calculated for $C_{21}H_{24}Cl_2N_2O_4$: C 57.4; H 5.51; N 6.38; Cl 16.14.

T.L.C.:
mobile phase: benzene:MeOH (80:20) $R_f = 0.38$.

IR ($CHCl_3$):
$\nu$(NH) 3300 cm$^{-1}$ amide, $\nu$(C=O) 1670 cm$^{-1}$ amide.

NMR ($CDCl_3$) $\delta$ppm:
1.18—3H—t—J=6 Hz (O—CH$_2$—$\underline{CH_3}$)
2.16—3H—s—(CH$_3$—CO—)
8.47—1H—s—(—CONH—)

The following compounds were prepared using the same procedure:

N-(β-ethoxyethyl)-N-[4-phenoxy-(4'-propionylamino)-benzyl]-dichloroacetamide, m.p. 100°-103° C. (benzene, petrolium ether).

Elemental analysis:
found: C 58.1; H 5.75; N 6.08; Cl 15.49.
calculated for $C_{22}H_{26}Cl_2N_2O_4$: C 58.3; H 5.78; N 6.18; Cl 15.63.

T.L.C.:
mobile phase $CHCl_3$:MeOH (190:10) $R_f = 0.47$.

I.R. ($CHCl_3$):
$\nu$(NH) 3400 cm$^{-1}$ amide, $\nu$(C=O) 1670 cm$^{-1}$ amide.

NMR ($CDCl_3$) $\delta$ppm:
1.18—3H—t—J=6 Hz (O—CH$_2$—$\underline{CH_3}$)
1.20—3H—t—($\underline{CH_3}$—CH$_2$—CO)
6.8-7.6—9H—m—(aromatic H and —COCHCl$_2$)
8.0—1H—s—(—CONH—).

N-(β-ethoxyethyl)-N-[4-phenoxy-(4'-trifluoroacetamido)-benzyl]-dichloroacetamide, m.p. 110°-113° C. (benzene-ligroin).

Elemental analysis:
found: C 51.21; H 4.2; N 5.67.
calculated for $C_{21}H_{21}F_3Cl_2N_2O_4$: C 51.12; H 4.29; N 5.69.

T.L.C.:
mobile phase $CHCl_3$:MeOH (190:10) $R_f = 0.59$.

I.R.: $\nu$(NH) 3400 cm$^{-1}$ amide, $\nu$(C=O) 1725 cm$^{-1}$ amide sec, $\nu$(C=O) 1670 cm$^{-1}$ amide tert.

NMR ($CDCl_3$) $\delta$ppm:
1.18—3H—t—J=6 Hz (O—CH$_2$—$\underline{CH_3}$)
6.8-7.7—9H—m—(aromatic H and COCHCl$_2$)
8.3—1H—s—(CONH).

EXAMPLE 4

1.2 ml of pivaloyl chloride was added to a stirred and cooled (0° C.) solution of 2.5 g of N-(β-ethoxyethyl)-N-[4-phenoxy-(4'-amino)-benzyl]-dichloroacetamide in 25 ml of anhydrous pyridine. The reaction was stirred for 15 minutes at 0° C. and 48 hours at room temperature. It was then evaporated to dryness under reduced pressure.

The residue was taken up in water and stirred for a few hours at room temperature. The mixture was then reduced in volume under reduced pressure, added to water and extracted several times with $CHCl_3$. The combined organic extract was washed with water, dried over $CaCl_2$, and evaporated to dryness. To a solution of the oily residue in 50 ml of ethanol was then added dropwise 200 ml of water. A solid formed overnight (5° C.) which was isolated by filtration and triturated with benzene and then pentane to give 2.8 g of N-(β-ethoxyethyl)-N-[4-phenoxy-(4'-pivaloylamino)-benzyl]-dichloroacetamide, m.p. 91°-93° C.

Elemental analysis:
found: C 55.77; H 6.27; N 5.74; Cl 14.64.
calculated for $C_{24}H_{23}Cl_2N_2O_4$: C 60.00; H 6.23; N 5.71; Cl 14.73.

T.L.C.:
mobile phase $CHCl_3$:MeOH (190:10) $R_f = 0.77$

I.R. ($CHCl_3$), $\nu$(NH) 3400 cm$^{-1}$ amide, $\nu$(C=O) 1670 cm$^{-1}$ amide.

NMR ($CDCl_3$) $\delta$ppm:
1.18—3H—t—J=6 Hz (O—CH$_2$—$\underline{CH_3}$)
1.33—9H—s—(CH$_3$)$_3$
6.88-7.6—9H—m—(aromatic H and COCHCl$_2$)
7.44—1H—s—(CONH)

The following compounds were prepared using the same procedure:

N-(β-ethoxyethyl)-N-[4-phenoxy-(4'-chloroacetamido)-benzyl]-dichloroacetamide;

N-(β-ethoxyethyl)-N-[4-phenoxy-(4'-dichloroacetamido)-benzyl]-dichloroacetamide;

N-(β-ethoxyethyl)-N-[4-phenoxy-(4'-benzoylamino)-benzyl]-dichloroacetamide;

EXAMPLE 5

0.1 g of p-toluenesulfonic acid was added to a solution of 2.5 g of N-(β-ethoxyethyl)-N-[4-phenoxy-(4'-amino)benzyl]-dichloroacetamide and 1.15 ml of ethyl orthoformate in 35 ml of absolute ethanol; the resulting mixture was then refluxed for 15 minutes. A slow distillation was then effected with a Raschig-ring filled column until all the ethanol distilled (approximately 3 hours). 0.5 N hydrochloride acid in 50% aqueous methanol was then added. After 24 hours at room temperature, the solution was reduced in volume, brought to pH 9 and extracted with $CHCl_3$. The organic extract was washed with water, dried over $Na_2SO_4$ and evaporated to give 2.2 g of N-(β-ethoxyethyl)-N-[4-phenoxy-(4'-ethylamino)-benzyl]-dichloroacetamide.

Elemental analysis:
found: C 59.25; H 6.18; N 6.65.
calculated for $C_{21}H_{26}N_2Cl_2O_3$: C 59.29; H 6.15; N 6.58.

I.R. ($CHCl_3$):
$\nu$(C=O) 1675 cm$^{-1}$ amide

NMR ($CDCl_3$) $\delta$ppm:
1.16—6H—t—(O—CH$_2$—$\underline{CH_3}$ and N—CH$_2$—$\underline{CH_3}$)
6.8-7.7—9H—m—(aromatic H and CO—CHCl$_2$)

The following compounds were prepared using the same procedure:

N-(β-ethoxyethyl)-N-[4-phenoxy-(4'-methylamino)-benzyl]-dichloroacetamide;

N-(β-ethoxyethyl)-N-[4-phenoxy-(4'-n-butylamino)-benzyl]-dichloroacetamide;

N-(β-ethoxyethyl)-N-[4-phenoxy-(4'-t-butylamino)-benzyl]-dichloroacetamide.

EXAMPLE 6

A solution of 2.5 g of N-(β-ethoxyethyl)-N-[4-phenoxy-(4'-amino)-benzyl]dichloroacetamide, 1.4 g of ethyl bromide and 1.4 g of triethylamine in 60 ml of anhydrous benzene was refluxed for 24 hours. The reaction mixture was then filtered; the filtrate was washed with water, dried over $Na_2SO_4$ and evaporated to dryness to give 2.1 g of N-(β-ethoxyethyl)-N-[4-phenoxy-(4'-diethylamino)-benzyl]-dichloroacetamide.

Elemental analysis:
found C 60.81; H 6.71; N 6.19.

calculated for $C_{23}H_{30}N_2Cl_2O_3$: C 60.92; H 6.67; N 6.18.

IR (CHCl$_3$):
$\nu$(C=O) 1680 cm$^{-1}$ amide,

NMR (CDCl$_3$) $\delta$ppm:
1.16—9H—t—(O—CH$_2$—C$\underline{H}_3$ and N—(CH$_2$C$\underline{H}_3$)$_2$
6.8-7.6—9H—m—(aromatic H and COCHCl$_2$).

N-($\beta$-ethoxyethyl)-N-[4-phenoxy-(4'-dimethylamino)-benzyl]-dichloroacetamide was prepared according to the same procedure.

EXAMPLE 7

2.6 ml of pivaloyl chloride was added at 0° C. to 3.5 g of tert-butyloxycarbonylglycine and 3 ml of triethylamine in 20 ml of anhydrous acetone. After 10 minutes of stirring at 0° C., a solution of N-($\beta$-ethoxyethyl)-N-[4-phenoxy-(4'-amino)-benzyl]-dichloroacetamide (8 g in 30 ml acetone) was added. The reaction mixture was then stirred for 3 hours at room temperature, filtered and evaporated to dryness. The residue was then crystallized from ethanol to afford 8 g of N-($\beta$-ethoxyethyl)-N-[4-phenoxy-(4'-tertbutoxycarbonylglycinylamino)-benzyl]-dichloroacetamide, m.p. 138°-140° C.

Elemental analysis:
found: C 59.00; H 6.18; N 12.95; Cl 7.6,
calculated for $C_{25}H_{33}N_3Cl_2O_6$: C 59.38; H 6.14; N 13.07; Cl 7.75.

A 3% solution of hydrochloric acid in ethyl acetate was then added to a solution of 6 g of the tert-butoxycarbonyl derivative described above in 80 ml of ethanol. The reaction mixture was held at room temperature for 4 hours. Subsequent addition of anhydrous ethyl ether at 4° C. caused precipitation of a solid which was then isolated by filtration. Washing with anhydrous ethyl ether and drying gave 5.2 g of N-($\beta$-ethoxyethyl)-N-[4-phenoxy-(4'-glycinylamino)-benzyl]-dichloroacetamide hydrochloride.

Elemental analysis:
found: C 51.38; H 5.39; N 8.44; Cl 21.39,
calculated for $C_{21}H_{26}N_3Cl_3O_4$: C 51.42; H 5.35; N 8.58; Cl 21.62.

T.L.C.:
mobile phase CHCl$_3$:MeOH:NH$_4$OH (32%) (170:30:2) R$_f$=0.43.

NMR (CDCl$_3$) $\delta$ppm:
1.08—3H—t—(O—CH$_2$—C$\underline{H}_3$)
3.81—2H—s—(C$\underline{H}_2$—NH$_2$) 6.8-7.8—9-H—m—(aromatic and —COCHCl$_2$)
8.4—3H—broad s—(NH$_2$.HCl)
10.98—1H—s—(CON$\underline{H}$Ph)

IR (KBr):
$\nu$(N—H) 3400 cm$^{-1}$
$\nu$(C=O) 1665 cm$^{-1}$
$\nu$(C—O—C) aromatic 1235 cm$^{-1}$
$\nu$(C—O—C) aliphatic 1120 cm$^{-1}$.

EXAMPLE 8

1.92 ml of pivaloyl chloride was added at 0° C. to a solution of tert-butoxycarbonyl-(S)-norvaline (3.2 g) and triethylamine (2.2 ml) in 50 ml of anhydrous acetone. After 10 minutes of stirring at 0° C., a solution of 5.8 g of N-($\beta$-ethoxyethyl)-N-[4-phenoxy-(4'-amino)-benzyl]-dichloroacetamide in 20 ml of anhydrous acetone was added. The reaction mixture was then stirred for 3 hours at room temperature, filtered and evaporated to dryness. The residue was taken up in methylene chloride and then washed successively with 5% citric acid solution, 2% sodium bicarbonate and water. Drying over anhydrous sodium sulfate, filtration and evaporation afforded 6.5 g of N-($\beta$-ethoxyethyl)-N-[4-phenoxy-(4'-tert-butoxycarbonyl-(S)-norvalinylamino)-benzyl]-dichloroacetamide as a viscous oil.

Elemental analysis:
found: C 58.36; H 6.60; N 6.99; Cl 12.00.
calculated for $C_{29}H_{30}N_3Cl_2O_6$: C 58.38; H 6.59; N 7.05; Cl 11.9.

NMR (CDCl$_3$) $\delta$ppm:
0.94—3H—t—(C$\underline{H}_3$—CH$_2$—CH$_2$)
1.17—3H—t—(C$\underline{H}_3$—CH$_2$—O)
1.43—9H—s—(C$\underline{H}_3$)$_3$C—
3.47—2H—q—(CH$_3$—C$\underline{H}_2$—O—)
4.66—2H—s—(Ph—C$\underline{H}_2$—N)
5.62—1H—d—(CO—N$\underline{H}$—CH$_2$—)
6.95—1H—s—(CO—C$\underline{H}$Cl$_2$)
9.15—1H—broad s—(CON$\underline{H}$—Ph)

To a solution of the above tert-butoxycarbonyl derivative (6 g in 80 ml of anhydrous ethanol) was added a 5% solution of hydrochloric acid in anhydrous ethyl acetate. After 6 hours at room temperature, the solution was evaporated to dryness under reduced pressure. The residue was then taken up in absolute ethanol and the solution reevaporated. Washing with benzene and ethyl ether gave 4 g of N-($\beta$-ethoxyethyl)-N-[4-phenoxy-(4'-(S)-norvalinylamino)-benzyl]-dichloroacetamide hydrochloride.

Elemental analysis:
found: C 53.89; H 6.06; N 7.88; Cl 19.96.
calculated for $C_{24}H_{32}N_3ClO_4$: C 54.09; H 6.05; N 7.88; Cl 19.96.

T.L.C.:
mobile phase CHCl$_3$:MeOH:NH$_4$OH (32%) (190:10:1) R$_f$=0.42.

IR (KBr)
$\nu$(N$^+$—H) 3200-2850 cm$^{-1}$
$\nu$(C=O) 1670 cm$^{-1}$
$\nu$(C—N) and (N—H) 1550 cm$^{-1}$
$\nu$(C—O—C) aromatic 1240 cm$^{-1}$
$\nu$(C—O—C) aliphatic 1120 cm$^{-1}$.

The following compounds were prepared using the same procedure:

N-($\beta$-ethoxy-ethyl)-N-[4-phenoxy-(4'-norvalinylamino)-benzyl]-dichloroacetamide;

N-($\beta$-ethoxy-ethyl)-N-[4-phenoxy-(4'-alanylamino)-benzyl]-dichloroacetamide;

N-($\beta$-ethoxy-ethyl)-N-[4-phenoxy-(4'-valinylamino)-benzyl]-dichloroacetamide;

N-($\beta$-ethoxy-ethyl)-N-[4-phenoxy-(4'-leucinylamino)-benzyl]-dichloroacetamide;

N-($\beta$-ethoxy-ethyl)-N-[4-phenoxy-(4'-$\beta$-alanylamino)-benzyl]-dichloroacetamide;

N-($\beta$-ethoxy-ethyl)-N-[4-phenoxy-(4'-$\gamma$-aminobutyrylamino)-benzyl]-dichloroacetamide;

N-($\beta$-ethoxy-ethyl)-N-[4-phenoxy-(4'-lactoylamino)-benzyl]-dichloroacetamide;

N-($\beta$-ethoxy-ethyl)-N-[4-phenoxy-(4'-hydroxyacetamido)-benzyl]-dichloroacetamide;

N-($\beta$-ethoxy-ethyl)-N-[4-phenoxy-(4'-$\alpha$-hydroxybutyrylamino)-benzyl]-dichloroacetamide.

EXAMPLE 9

A solution of butyloxycarbonyl-(S)-methionine (3.36 g) and (Et)$_3$N (2 ml) in anhydrous acetone (45) ml was cooled to 0° C. and pivaloyl chloride (1.83 ml) added. The reaction mixture was stirred for 10 minutes at 0° C. and then a solution of N-($\beta$-ethoxyethyl)-N-[4-phenoxy- (4'-amino)-benzyl]-dichloroacetamide (5.3 g) in anhydrous acetone (20 ml) was added.

After three hours of stirring at room temperature, the reaction mixture was filtered and the filtrate evaporated to dryness. The residue was taken up in methylene chloride and this solution was washed first with 5% citric acid solution, then 2% sodium bicarbonate and then water, dried over anhydrous sodium sulfate, filtered and evaporated. The yield was 6.7 g of N-(β-ethoxyethyl)-N-[4-phenoxy-(4'-tert-butyloxycarbonyl-(S)-methionylamino)-benzyl]-dichloroacetamide, as an oil.

Elemental analysis:
found: C 55.31; H 6.25; N 6.72; Cl 11.21; S 5.04;
calculated for $C_{29}H_{40}N_3Cl_3O_6S$: C 55.41; H 6.25; N 6.68; Cl 11.28; S 5.10.

A solution of the oil (70 ml) in anhydrous ethanol (80 ml) had added to it a 5% solution of hydrochloric acid in anhydrous ethyl acetate. After 6 hours at room temperature, the solution was evaporated to dryness under vacuum, redissolved in absolute ethanol and again evaporated to dryness. After washing with benzene and with anhydrous ethyl ether, 5.3 g of N-(β-ethoxyethyl)-N-[4-phenoxy-(4'-(S)-methiomylamino)-benzyl]-dichloroacetamide hydrochloride were obtained.

Elemental analysis:
found: C 51.12; H 5.74; N 7.46; Cl 18.64; S 5.62.
calculated for $C_{24}H_{32}N_3Cl_3O_4S$: 51.02; H 5.73; N 7.44; Cl 18.83; S 5.67.

IR $(CHCl_3)$ $\nu(C=O)$ 1670 $cm^{-1}$ $\nu(C-O-C)$ aromatic 1240 $cm^{-1}$ $\nu(C-O-C)$ aliphatic 1120 $cm^{-1}$.

NMR $(CDCl_3)$ [referred to the free base] δ ppm:
1.18—3H—t—$(O-CH_2-\underline{CH_3})$
1.96—2H—m—$(-\underline{CH_2}-S-CH_3)$
2.13—3H—s—$(-CH_2-S-\underline{CH_3})$
2.40—2H—broad s—$(-\underline{NH_2})$
4.67—2H—s—$(Ph-\underline{CH_2}N-)$
6.93—1H—s—$(CO-\underline{CH}-Cl_2)$
9.81—1H broad s $(CO-\underline{NH}-Ph)$.

The following compounds were prepared using the same procedure:
N-(β-ethoxyethyl)-N-[4-phenoxy-(4'-lysinylamino)-benzyl]-dichloroacetamide;
N-(β-ethoxyethyl)-N-[4-phenoxy-(4'-serinylamino)-benzyl]-dichloroacetamide;
N-(β-ethoxyethyl)-N-[4-phenoxy-(4'-tyrosinylamino)-benzyl]-dichloroacetamide;
N-(β-ethoxyethyl)-N-[4-phenoxy-(4'-aspartylamino)-benzyl]-dichloroacetamide;
N-(β-ethoxyethyl)-N-[4-phenoxy-(4'-asparaglyamino)-benzyl]-dichloroacetamide;
N-(β-ethoxyethyl)-N-[4-phenoxy-(4'-glutamylamino)-benzyl]-dichloroacetamide;
N-(β-ethoxyethyl)-N-[4-phenoxy-(4'-glutaminylamino)-benzyl]-dichloroacetamide;
N-(β-methoxyethyl)-N-[4-phenoxy-(4'-methionylamino)-benzyl]-dichloroacetamide.

EXAMPLE 10

To a solution of N-(β-ethoxyethyl)-N-[4-phenoxy-(4'-amino)-benzyl]-dichloroacetamide (2 g) in methylene chloride (30 ml) were added 0.4 ml of ethyl isocyanate. The solution was refluxed for 3 hours, filtered, washed with water, dried and evaporated to dryness. The residue was crystallized from ethyl acetate to give 1.9 g of N-(β-ethoxyethyl)-N-{4-phenoxy-[4'-(N-ethyl-carbamoyl)-amino]-benzyl}-dichloroacetamide, m.p. 119°–121° C.

Elemental analysis:
found: C 56.52; H 5.61; N 8.96; Cl 15.12,
calculated for $C_{22}H_{27}N_2O_4Cl_2$: C 56.4; H 5.57; N 8.98; Cl 15.15.

NMR $(CDCl_3)$ δ ppm:
1.1—3H—t $(NHCH_2-\underline{CH_3})$
1.17—3H—t $(-O-CH_2-\underline{CH_3})$
4.66—2H—s $(Ph-\underline{CH_2}-N-)$
5.9—1H—broad

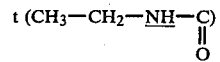
t $(CH_3-CH_2-\underline{NH}-C)$ 6.65–7.4 9H m (aromatic, $\underline{CH}Cl_2$)
7.83 1H

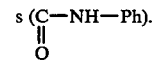
s $(C-NH-Ph)$.

The following compound was prepared by an analogous procedure: N-(β-ethoxyethyl)-N-{4-phenoxy-[4'-(N-methylcarbamoyl)-amino]-benzyl}-dichloroacetamide.

EXAMPLE 11

To a solution of N-(β-ethoxyethyl)-N-[4-phenoxy(4'-amino)-benzyl]-dichloroacetamide (5.8 g) in anhydrous acetone (15 ml) were added, with shaking and at −10° C., first triethylamine (2.2 ml), and then, drop by drop, ethylchloroformiate (1.75 ml). The reaction mixture was stirred for 2 hours at room temperature and then filtered and evaporated the dryness. The residue was dissolved in ethyl acetate and the organic phase was washed with water, dried and re-evaporated. The residue was crystallized from benzene-petroleum ether to give 6.2 g of N-(β-ethoxyethyl)-N-[4-phenoxy-(4'-ethoxycarbonylamino)-benzyl]-dichloroacetamide, m.p. 104°–105° C.

Elemental analysis:
found: C 56.53; H 5.62; N 5.79; Cl 14.88,
calculated for $C_{22}H_{26}N_2C_2O_5$: C 56.25; H 5.58; N 5.96; Cl 15.10.

IR $(CHCl_3)$ $\nu(NH)$ 3430 $cm^{-1}$ $\nu(C=C)$ 1729 $cm^{-1}$ carbamate, $\nu(C=O)$ 1670 $cm^{-1}$ amide.

T.L.C.:
mobile phase ethyl ether $R_f=0.56$
NMR $(CDCl_3)$ δ ppm:
1.17—3H—t—$(CH_2-O-CH_2-\underline{CH_3})$

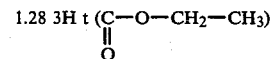
1.28 3H t $(C-O-CH_2-CH_3)$

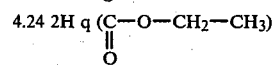
4.24 2H q $(C-O-CH_2-CH_3)$ 4.66—2H—s—$(Ph-\underline{CH_2}-N-)$
6.92—1H—s—$(COC\underline{H}-Cl_2)$.

EXAMPLE 12

To a reaction mixture containing N-(β-ethoxyethyl)-4-phenoxy-(4'-methyl-sulfonyl)-benzylamine hydrochloride (1.93 g), symmetric dichloroethane (25 ml) and 1 N NaOH (12 ml) were added, at 0° C. and with stirring, dichloroacetyl chloride (0.1 ml). The reaction mixture was kept for 10 min at 0° C. and then for one hour at room temperature. The organic phase was decanted off, washed with water, dried and evaporated to dryness. The residue was crystallized from ethyl acetate to give 1.97 g of N-(β-ethoxyethyl)-N-[4-phenoxy(4'-methylsulfonyl)-benzyl]-dichloroacetamide, m.p. 131°–132° C.

Elemental analysis:
found: C 52.14; H 5.06; N 3.01; Cl 15.33
calculated for $C_{20}H_{23}NCl_2O_5S$: C 52.17; H 5.035; N 3.04; Cl 15.40

IR $(CHCl_3)$ $\nu(C=O)$ 1680–1650 cm$^{-1}$ $\nu(S-O_2)$ 1322–1290 cm$^{-1}$ 1150–1110 cm$^{-1}$.

T.L.C.:
mobile phase $CHCl_3$:MeOH = 195:5
$R_f = 0.56$

NMR $(CDCl_3)$ δ ppm:
1.17—3H—t—$(CH_2—\underline{CH_3})$
3.07—3H—s—$(SO_2\underline{CH_3})$
4.75—2H—s—$(Ph—\underline{CH_2}—N—)$
6.93—1H—s—$(CO—\underline{CH}—Cl_2)$.

The N-(β-ethoxyethyl)-4-phenoxy-(4'-methylsulfonyl)-benzylamine hydrochloride used as starting material was prepared as follows: To a solution of 4-phenoxy-(4'-methylsulfonyl)-benzylchloride (3 g) in methylene chloride (15 ml) were added, at 0° C. and with stirring, portions of β-ethoxyethylamine (total amount 3.88 g). After 4 hours of stirring at room temperature, 100 ml of water were added and the mixture extracted with ethyl acetate. The organic phase was washed with water and dried and then gaseous hydrochloric acid was bubbled through. The solid precipitate was filtered out and recrystallized from isopropanol to give 2.9 g of N-(β-ethoxyethyl)-4-phenoxy-(4'-methylsulfonyl)-benzylamine hydrochloride, m.p. 191°–193° C.

Elemental analysis:
found: C 56.02; H 6.25; N 3.65; Cl 9.14,
calculated for $C_{18}H_{24}NClO_4S$: C 56.02; H 6.27; N 3.63; Cl 9.19.

The 4-phenoxy-(4'-methylsulfonyl)-benzyl chloride used in the above reaction was prepared by chloromethylation of 4-methylsulfonyl-diphenyl ether by the following procedure: A mixture of 4-methylsulfonyl-diphenyl ether (6.2 g), trioxymethylene (1.3 g), and anhydrous $ZnCl_2$ (3.4 g) in glacial acetic acid (35 ml) was saturated at 10° C. with gaseous HCl for 2 hours and at 40° C. for another 2 hours. The reaction mixture was poured into a mixture of water and ice and then extracted with ethyl ether. The organic phase was washed with water and with a 5% $NaHCO_3$ solution, then dried and evaporated to dryness. The residue was crystallized from 90% ethanol to give 5.5 g of 4-phenoxy-(4'-methylsulfonyl)-benzyl chloride, m.p. 115°–118° C.

Elemental analysis:
found: C 57.07; H 4.44; Cl 11.78; S 10.86.
calculated for $C_{14}H_{13}ClO_3S$: C 56.65; H 4.41; Cl 11.95; S 10.80.

EXAMPLE 13

To a solution of chlorosulfonyl isocyanate (1.4 g) in acetonitrile (30 ml) were added, at 0° C. and with stirring, a solution of N-(β-ethoxyethyl)-N-[4-phenoxy-(4'-amino)-benzyl]-dichloroacetamide (4 g) in acetonitrile (30 ml). The reaction mixture was kept at 0° C. for three hours and then poured, with cooling, into 300 ml of 0.1 N sulfuric acid. The solution was neutralized with $NaHCO_3$ and then extracted with $CHCl_3$ and the organic phase was washed with water, dried and evaporated to dryness. The yield was 4.5 g of N-(β-ethoxyethyl)-N-[4-phenoxy-(4'-ureido)-benzyl]-dichloroacetamide, m.p. 60°–65° C.

Elemental analysis:
found: C 54.2; H 5.25; N 9.48; Cl 16.08;
calculated for $C_{20}H_{23}N_8Cl_2O_4$: C 54.5; H 5.22; N 9.52; Cl 16.13.

NMR $(CDCl_3)$ δ ppm:
1.17—3H—t—$(O—CH_2—\underline{CH_3})$
4.66—2H—s—$(Ph—\underline{CH_2}—N—)$
5.3—2H—s $(H_2N—\underset{\underset{O}{\|}}{C}—NH)$ 6.65–7.4—9H—m (aromatic, $\underline{CH}Cl_2$)
7.9—1H—s $(\underset{\underset{O}{\|}}{C}—NH—Ph)$.

EXAMPLE 14

The following are examples of pharmaceutical compositions for use in therapy:

Pills: Each tablet contains 200 mg of N-(β-ethoxyethyl)-N-[4-phenoxy-(4'-acetamido)-benzyl]-dichloroacetamide, 2.3 mg of methylcellulose, 17.4 mg of starch, 25.3 mg of microcrystalline cellulose, 5 mg of stearic acid.

Syrup: N-(β-ethoxyethyl)-N-[4-phenoxy-(4'-acetamido)-benzyl]-dichloroacetamide (2 g), 1 g of gum-tragacanth, 0.135 g of methyl p-hydroxybenzoate, 0.015 g of propyl p-hydroxybenzoate, 0.2 g of Tween 20, 5 g of glycerine 30 Be, 50 g of sucrose, flavoring as needed, demineralized water to 100 ml.

EXAMPLE 15

Analogously to Example 14 tablets and syrups containing the other compounds of the invention, in particular the compounds:

N-(β-ethoxy-ethyl)-N-[4-phenoxy-(4'-amino)-benzyl]-dichloroacetamide;

N-(β-ethoxy-ethyl)-N-[4-phenoxy-(4'-(S)-norvalinylamino)-benzyl]-dichloroacetamide chloride;

N-(β-ethoxy-ethyl)-N-[4-phenoxy-(4'-glycinylamino)-benzyl]-dichloroacetamide;

N-(β-ethoxy-ethyl)-N-[4-phenoxy-(4'-(S)-methionylamino)-benzyl]-dichloroacetamide;

N-(β-ethoxy-ethyl)-N-[4-phenoxy-(4'-methylsulphonyl)-benzyl]-dichloroacetamide, were prepared.

We claim:

1. A compound of the formula $$Y-\underset{}{\bigcirc}-O-\underset{}{\bigcirc}-CH_2-\underset{COCHCl_2}{N}-CH_2-CH_2-O-R$$

wherein
R is $C_1$–$C_6$ alkyl;
Y is (a)

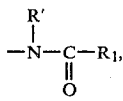

wherein
R' is hydrogen or $C_1$–$C_6$ alkyl, and
$R_1$ is
(1) $C_1$–$C_{12}$ alkyl
(a') unsubstituted or
(b') substituted by one or more substituents selected from the group consisting of (1) halogen, (2) carboxy, (3) carbamoyl, (4) methylthio, (5) —OR', wherein R' is hydrogen or $C_1$–$C_6$ alkyl, (6)

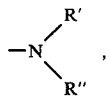

wherein
R' and R" are independently hydrogen or $C_1$–$C_6$ alkyl and (7) phenyl, which is unsubstituted or substituted by one or more hydroxy groups; or
(2) phenyl,
(a') unsubstituted or
(b') substituted by one or more substituents selected from the group consisting of (1') halogen, (2'), $C_1$–$C_6$ alkyl, (3') trihalo-$C_1$–$C_6$—alkyl, (4') nitro, (5')—OR' wherein R' is hydrogen or $C_1$–$C_6$ and (6')

wherein R' and R" are independently hydrogen or $C_1$–$C_6$ alkyl
or a pharmaceutically or veterinarily acceptable salt thereof.

2. A compound of the formula

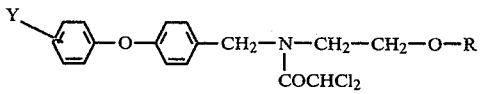

wherein
R is $C_1$–$C_3$ alkyl;
Y is

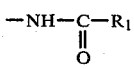

wherein
$R_1$ is (a') $C_1$–$C_6$ alkyl unsubstituted or substituted by one or more substituents selected from the group consisting of halogen, methylthio, carboxy, carbamoyl, unsubstituted phenyl, hydroxy, amino and phenyl; or a pharmaceutically or veterinarily acceptable salt thereof.

3. A compound selected from the group-consisting of:
N-(β-ethoxy-ethyl)-N-[4-phenoxy-(4'-acetamido)-benzyl]-dichloroacetamide;
N-(β-ethoxy-ethyl)-N-[4-phenoxy-(4'-chloroacetamido)-benzyl]-dichloroacetamide;
N-(β-ethoxy-ethyl)-N-[4-phenoxy-(4'-dichloroacetamido)-benzyl]-dichloroacetamide;
N-(β-ethoxy-ethyl)-N-[4-phenoxy-(4'-trifluoroacetamido)-benzyl]-dichloroacetamide;
N-(β-ethoxy-ethyl)-N-[4-phenoxy-(4'-propionyiamino)-benzyl]-dichloroacetamide;
N-(β-ethoxy-ethyl)-N-[4-phenoxy-(4'-pyvaloylamino)-benzyl]-dichloroacetamide;
N-(β-ethoxy-ethyl)-N-[4-phenoxy-(4'-benzoylamino)-benzyl]-dichloroacetamide;
N-(β-ethoxy-ethyl)-N-[4-phenoxy-(4'-glycinylamino)-benzyl]-dichloroacetamide;
N-(β-ethoxy-ethyl)-N-[4-phenoxy-(4'-norvalinylamino)-benzyl]-dichloroacetamide;
N-(β-ethoxy-ethyl)-N-[4-phenoxy-(4'-alanylamino)-benzyl]-dichloroacetamide;
N-(β-ethoxy-ethyl)-N-[4-phenoxy-(4'-valinylamino)-benzyl]-dichloroacetamide;
N-(β-ethoxy-ethyl)-N-[4-phenoxy-(4'-leucinylamino)-benzyl]-dichloroacetamide;
N-(β-ethoxy-ethyl)-N-[4-phenoxy-(4'-β-alanylamino)-benzyl]-dichloroacetamide;
N-(β-ethoxy-ethyl)-N-[4-phenoxy-(4'-γ-aminobutyrylamino)-benzyl]-dichloroacetamide;
N-(β-ethoxy-ethyl)-N-[4-phenoxy-(4'-lysinylamino)-benzyl]-dichloroacetamide;
N-(β-ethoxy-ethyl)-N-[4-phenoxy-(4'-serinylamino)-benzyl]-dichloroacetamide;
N-(β-ethoxy-ethyl)-N-[4-phenoxy-(4'-methionylamino)-benzyl]-dichloroacetamide;
N-(β-ethoxy-ethyl)-N-[4-phenoxy-(4'-tyrosinylamino)-benzyl]-dichloroacetamide;
N-(β-ethoxy-ethyl)-N-[4-phenoxy-(4'-aspartylamino)-benzyl]-dichloroacetamide;
N-(β-ethoxy-ethyl)-N-[4-phenoxy-(4'-asparagylamino)-benzyl]-dichloroacetamide;
N-(β-ethoxy-ethyl)-N-[4-phenoxy-(4'-glutamylamino)-benzyl]-dichloroacetamide;
N-(β-ethoxy-ethyl)-N-[4-phenoxy-(4'-glutaminylamino)-benzyl]-dichloroacetamide;
N-(β-ethoxy-ethyl)-N-[4-phenoxy-(4'-lactoylamino)-benzyl]-dichloroacetamide;
N-(β-ethoxy-ethyl)-N-[4-phenoxy-(4'-hydroxyacetamido)-benzyl]-dichloroacetamide;
N-(β-ethoxy-ethyl)-N-[4-phenoxy-(4'-α-hydroxybutyrylamino)-benzyl]-dichloroacetamide;
or the pharmaceutically or veterinarily acceptable salt thereof.

4. A pharmaceutical composition suitable for the treatment of amebiasis, comprising a therapeutically effective amount of a compound of any one of claims 1, 2, or 3 and a pharmaceutically acceptable carrier.

5. Method of treating a patient suffering from amebiasis, said method comprising administering to said patient a therapeutically effective amount of a compound of any one of claims 1, 2 or 3.

6. The compound N-(β-ethoxy-ethyl)-N-[4-phenoxy-(4'-acetamido)-benzyl]-dichloroacetamide.

7. A pharmaceutical composition suitable for the treatment of amebiasis, comprising a therapeutically effective amount of the compound of claim 6, and a pharmaceutically acceptable carrier.

8. Method of treating a patient suffering from amebiasis, said method comprising administering to said patient a therapeutically effective amount of the compound of claim 6.

* * * * *